US012590075B2

(12) United States Patent
Tohnai et al.

(10) Patent No.: US 12,590,075 B2
(45) Date of Patent: Mar. 31, 2026

(54) REFINING METHOD

(71) Applicant: NGK Insulators, Ltd., Nagoya (JP)

(72) Inventors: Norimitsu Tohnai, Suita (JP); Daiki Kato, Nagoya (JP); Yoshio Kondo, Nagoya (JP); Kazunari Yamada, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 551 days.

(21) Appl. No.: 18/147,229

(22) Filed: Dec. 28, 2022

(65) Prior Publication Data

US 2023/0150957 A1 May 18, 2023

Related U.S. Application Data

(63) Continuation of application No. PCT/JP2021/025388, filed on Jul. 6, 2021.

(30) Foreign Application Priority Data

Jul. 13, 2020 (WO) .................. PCT/JP2020/027266

(51) Int. Cl.
| | |
|---|---|
| *C07D 277/56* | (2006.01) |
| *C07C 51/43* | (2006.01) |
| *C07C 227/42* | (2006.01) |
| *C07D 223/26* | (2006.01) |
| *C30B 7/02* | (2006.01) |
| *C07D 277/30* | (2006.01) |

(52) U.S. Cl.
CPC ............ *C07D 277/56* (2013.01); *C07C 51/43* (2013.01); *C07C 227/42* (2013.01); *C07D 223/26* (2013.01); *C30B 7/02* (2013.01); *C07B 2200/13* (2013.01); *C07D 277/30* (2013.01)

(58) Field of Classification Search
CPC ....... C07C 51/43; C01D 9/0031; C30B 29/54; B01D 9/005
See application file for complete search history.

(56) References Cited

U.S. PATENT DOCUMENTS

| | | | |
|---|---|---|---|
| 2003/0153089 A1 | 8/2003 | Kuil et al. | |
| 2008/0293946 A1 | 11/2008 | Cheng | |
| 2010/0317702 A1 | 12/2010 | Piran et al. | |
| 2013/0137734 A1 | 5/2013 | Hotter et al. | |
| 2013/0187050 A1 | 7/2013 | Takebe et al. | |
| 2014/0093563 A1* | 4/2014 | Srivastava ........... | A61K 9/2054 |
| | | | 424/465 |
| 2016/0157300 A1 | 6/2016 | Komaki et al. | |
| 2016/0272641 A1 | 9/2016 | Abe et al. | |
| 2019/0194101 A1 | 6/2019 | Niwa et al. | |

FOREIGN PATENT DOCUMENTS

| | | |
|---|---|---|
| CN | 103333064 A | 10/2013 |
| CN | 108530382 A | 9/2018 |
| EP | 1 172 646 A1 | 1/2002 |
| EP | 3 299 370 A1 | 3/2018 |
| EP | 3 501 636 A1 | 6/2019 |
| JP | 2003-319800 A | 11/2003 |
| JP | 2004-504596 A | 2/2004 |
| JP | 2004-267114 A | 9/2004 |
| JP | 2009-510163 A | 3/2009 |
| JP | 2012-529537 A | 11/2012 |
| JP | 5215505 B2 | 6/2013 |
| JP | 2014-189462 A | 10/2014 |
| JP | 6442355 B2 | 12/2018 |
| WO | 2015/053297 A1 | 4/2015 |
| WO | 2018/034305 A1 | 2/2018 |

OTHER PUBLICATIONS

Atsushi Sakurai, "Application of Metamaterial to Wavelength-Selective Thermal Radiation Control and Solar-Thermophotovoltaic Power Generation," *JSME TED Newsletter*, No. 74 (2014), pp. 7-10 (with English translation) (13 pages).

Junichi Takahara, "Thermal Engineering and Photonics: Thermal Radiation Spectrum Control Utilizing Metasurface," *JSME TED Newsletter*, No. 74 (2014), pp. 2-6 (with English translation) (15 pages).

Atsushi Sakurai, et al., "Ultranarrow-Band Wavelength-Selective Thermal Emission with Aperiodic Multilayered Metamaterials Designed by Bayesian Optimization," *ACS Central Science*, vol. 5 (2019), pp. 319-326 (8 pages).

International Search Report and Written Opinion (Application No. PCT/JP2021/025388) dated Sep. 21, 2021.

International Search Report and Written Opinion (Application No. PCT/JP2020/027266) dated Sep. 24, 2020.

Andrea Rodomonte et al., "Different Crystal Morphologies Arising from Different Preparation Methods of a Same Polymorphic Form May Result in Different Properties of the Final Materials: The Case of Diclofenac Sodium Trihydrate," *Journal of Pharmaceutical and Biomedical Analysis*, Elesevier B.V., Amsterdam, NL, vol. 48, No. 2, Sep. 29, 2008, pp. 477-481 (5 pages).

Extended European Search Report (Application No. 21841440.7) dated Jul. 26, 2024 (12 pages).

Extended European Search Report (Application No. 21843513.9) dated Jul. 26, 2024 (11 pages).

Extended European Search Report (Application No. 21843135.1) dated Jul. 26, 2024 (10 pages).

(Continued)

*Primary Examiner* — Kyle A Purdy
(74) *Attorney, Agent, or Firm* — BURR PATENT LAW, PLLC

(57) ABSTRACT

A refining method according to the present invention is a refining method for crystallizing a compound with at least one crystal form, including: setting, as a target wavelength, a specific infrared wavelength at which a specific crystal form precipitates from a solution of the compound dissolved in a solvent; and using an infrared radiation apparatus capable of emitting infrared radiation including the target wavelength to evaporate the solvent and precipitate the specific crystal form while irradiating the solution with infrared radiation including the target wavelength. The specific infrared wavelength is preferably set as the target wavelength based on an infrared absorption spectrum of the crystal form and the dissolution rate of the compound in the solvent.

6 Claims, 5 Drawing Sheets

(56) References Cited

OTHER PUBLICATIONS

English translation of the International Preliminary Report on Patentability (Chapter I) dated Jan. 26, 2023 (Application No. PCT/JP2021/025388).
U.S. Appl. No. 18/147,198, filed Dec. 28, 2022, Tohnai, et al.
U.S. Appl. No. 18/147,251, filed Dec. 28, 2022, Tohnai, et al.
Chinese Office Action (Application No. 202180023504.3) dated Nov. 3, 2023 (with English translation) (11 pages).
Pharmacy, FU ed., Beijing: Chinese Pharmaceutical Science Press, pp. 31-31, Jan. 2003 (5 pages).
International Search Report and Written Opinion (Application No. PCT/JP2021/0253789) dated Sep. 21, 2021 (9 pages).

English translation of the Internation Preliminary Report on Patentability (Chapter I) (Application No. PCT/JP2021/025389) dated Jan. 26, 2023 (6 pages).
International Search Report and Written Opinion (Application No. PCT/JP2021/025390) dated Sep. 21, 2021 (8 pages).
English translation of the International Preliminary Report on Patentability (Chapter I) (Application No. PCT/JP2021/025390) dated Jan. 26, 2023 (5 pages).
U.S. Appl. No. 19/050,247, filed Feb. 11, 2025, Tohnai et al.
Yuyama et al., "*Selective Fabricaion of α- and γ-Polymorphs of Glycine by Intense Polarized Continuous Wave Laser Beams,*" American Chemistry Society, Crystal Growth & Design, 2012 pp. 2427-2434 (8 pages).
U.S. Office Action dated Sep. 5, 2025 (U.S. Appl. No. 18/147,251).
U.S. Office Action dated Jun. 18, 2024 (U.S. Appl. No. 18/147,198).

* cited by examiner

Febuxostat

Loxoprofen

REFINING METHOD

BACKGROUND OF THE INVENTION

1. Field of the Invention

The present invention relates to a refining method.

2. Description of the Related Art

Distillation, recrystallization, chromatography, extraction, and the like are generally known as methods for refining a target organic compound. Patent Literature 1 discloses a method for refining an organic compound using a laser beam. In Patent Literature 1, to selectively produce a metastable substance from a solution of a substance containing a stable form and a metastable form as crystal forms, metastable crystals are selectively produced by emitting a laser beam into the solution to generate bubbles and form metastable crystal nuclei.

CITATION LIST

Patent Literature

PTL 1: JP 2014-189462 A

SUMMARY OF THE INVENTION

In Patent Literature 1, however, the laser beam is emitted to generate bubbles in the solution, and no attention is paid to light of an infrared absorption wavelength.

The present invention has been made to address such an issue and mainly aims to obtain a specific crystal form from a solution of a compound dissolved in a solvent.

A refining method according to the present invention is a refining method for crystallizing a compound with at least one crystal form that includes setting, as a target wavelength, a specific infrared wavelength at which a specific crystal form precipitates from a solution of the compound dissolved in a solvent; and using an infrared radiation apparatus capable of emitting infrared radiation including the target wavelength to evaporate the solvent and precipitate the specific crystal form while irradiating the solution with infrared radiation including the target wavelength.

This refining method can precipitate a specific crystal form from a solution of a compound dissolved in a solvent by adjusting the solvent for dissolving the compound and the infrared radiation emitted to the solution. The reason why a specific crystal form precipitates is not clear but is considered as described below. A compound with a plurality of crystal forms generally has a dissolution rate depending on the type of solvent. The dissolution rate is probably related to the ease of precipitation of crystals. Furthermore, a crystal form with higher infrared absorptivity probably has more active thermal vibrations and fewer crystal nuclei. It is therefore thought that the suitable conditions for precipitation of a specific crystal form depend on the solvent for dissolving the compound and the infrared radiation emitted to the solution.

DETAILED DESCRIPTION OF THE INVENTION

Figure 1:
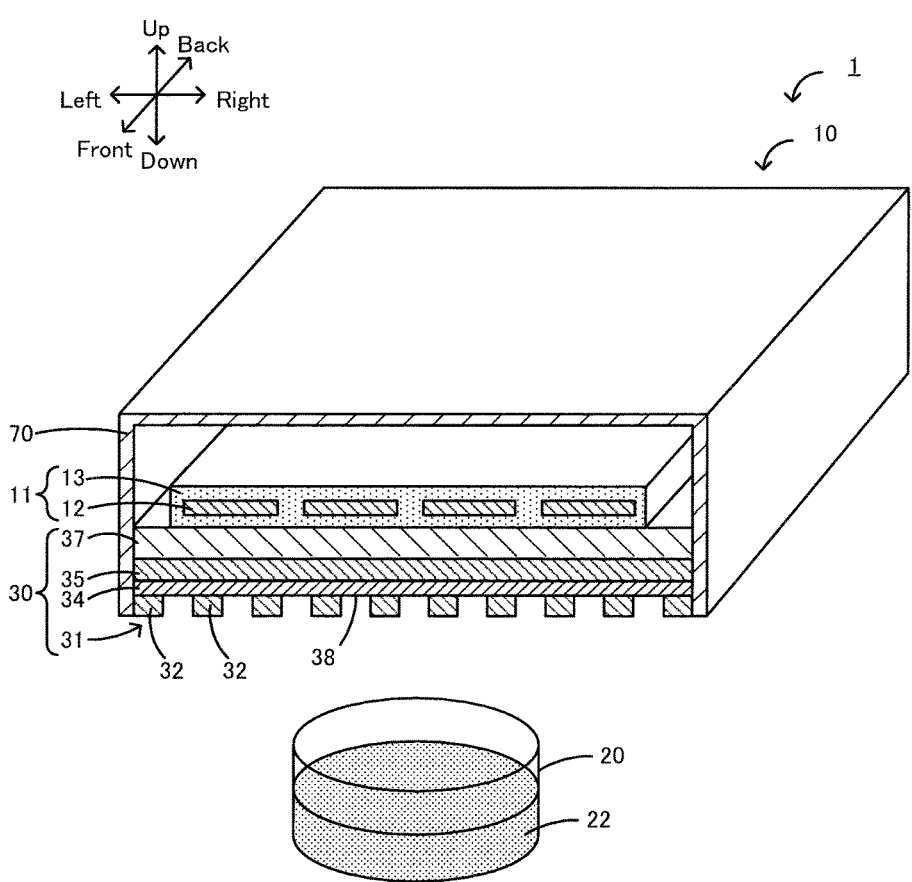
FIG. 1 is a perspective view of a refining apparatus 1 (partially in cross section).

Preferred embodiments of the invention are described in detail below.

A refining method according to the present embodiment is a refining method for crystallizing a compound with at least one crystal form that includes setting, as a target wavelength, a specific infrared wavelength at which a specific crystal form precipitates from a solution of the compound dissolved in a solvent; and using an infrared radiation apparatus capable of emitting infrared radiation including the target wavelength to evaporate the solvent and precipitate the specific crystal form while irradiating the solution with infrared radiation including the target wavelength.

The compound may have a plurality of crystal forms or a single crystal form.

In one example described below, a specific crystal form is precipitated by evaporating a solvent from a solution of a raw material of an organic compound X with four crystal forms a1, a2, b1, and b2 dissolved in the solvent. The specific crystal form is precipitated on the basis of the results of preliminary experiments. In a first preliminary experiment, it is assumed that a crystal form a1 is precipitated when a solution of the raw material of the organic compound X dissolved in a solvent p1 is irradiated with infrared radiation including a wavelength $\lambda 1$ [μm] to evaporate the solvent p1. In a second preliminary experiment, it is assumed that a crystal form a2 is precipitated when the solution of the raw material of the organic compound X dissolved in the solvent p1 is irradiated with infrared radiation including a wavelength $\lambda 2$ [μm] to evaporate the solvent p1. In a third preliminary experiment, it is assumed that a crystal form b1 is precipitated when the solution of the raw material of the organic compound X dissolved in a solvent p2 is irradiated with infrared radiation including a wavelength $\lambda 1$ [μm] to evaporate the solvent p2. In a fourth preliminary experiment, it is assumed that a crystal form b2 is precipitated when the solution of the raw material of the organic compound X dissolved in the solvent p2 is irradiated with infrared radiation including a wavelength $\lambda 2$ [μm] to evaporate the solvent p2. In such a preliminary experiment, to precipitate the crystal form a1, the solvent p1 used in the first preliminary experiment and infrared radiation including the wavelength $\lambda 1$ [μm] are employed. To precipitate the crystal form a2, the solvent p1 used in the second preliminary experiment and infrared radiation including the wavelength $\lambda 2$ [μm] are employed. To precipitate the crystal form b1, the solvent p2 used in the third preliminary experiment and infrared radiation including the wavelength $\lambda 1$ [μm] are employed. To precipitate the crystal form b2, the solvent p2 used in the fourth preliminary experiment and infrared radiation including the wavelength $\lambda 2$ [μm] are employed.

The wavelength $\lambda 1$ [μm] and the wavelength $\lambda 2$ [μm] are preferably set on the basis of an infrared absorption spectrum of a crystal form and the dissolution rate of a raw material in a solvent, more preferably on the basis of the stability of the crystal form, an infrared absorption spectrum of the crystal form, and the dissolution rate of the raw material in the solvent. Crystal forms often have different infrared absorption spectra and often have different absorptivities at a given wavelength. When a solution is irradiated with infrared radiation including a certain wavelength, a crystal form with a higher absorptivity at the wavelength has more active thermal vibration than crystal forms with a lower absorptivity, has fewer crystal nuclei, and is less likely to precipitate. On the other hand, it is thought that a crystal form that can easily form crystal nuclei is different between a solvent with a high dissolution rate of a raw material and a solvent with a low dissolution rate of a raw material. For example, a stable crystal form is often more difficult to dissolve than other crystal forms and is therefore likely to precipitate selectively in a solvent with a high dissolution rate. A less stable crystal form is likely to precipitate selectively in a solvent with a low dissolution rate. Thus, the wavelength $\lambda 1$ [$\mu$m] and the wavelength $\lambda 2$ [$\mu$m] are preferably set on the basis of an infrared absorption spectrum of a crystal form and the dissolution rate of a raw material in a solvent, more preferably on the basis of the stability of the crystal form, an infrared absorption spectrum of the crystal form, and the dissolution rate of the raw material in the solvent. For example, the infrared radiation including the wavelength $\lambda 1$ [$\mu$m] may be infrared radiation having a peak at the wavelength $\lambda 1$ [lam], and the infrared radiation including the wavelength $\lambda 2$ [$\mu$m] may be infrared radiation having a peak at the wavelength $\lambda 2$ [$\mu$m].

In the following example, a crystal form c is precipitated by evaporating a solvent q from a solution of an organic compound Y with the crystal form c dissolved in the solvent q. It is assumed that, in a preliminary experiment, the crystal form c precipitates when the solvent q is evaporated while the solution of the organic compound Y dissolved in the solvent q is irradiated with infrared radiation including a wavelength $\alpha$ [$\mu$m]. It is also assumed that the crystal form c does not precipitate and becomes amorphous when the solvent q is evaporated while the solution of the organic compound Y dissolved in the solvent q is not irradiated with infrared radiation. In such a case, to precipitate the crystal form c, the solvent q may be evaporated while the solution of the organic compound Y dissolved in the solvent q is irradiated with infrared radiation including a wavelength $\alpha$ [$\mu$m]. For example, the infrared radiation including the wavelength $\alpha$ [$\mu$m] may be infrared radiation having a peak at the wavelength $\alpha$ [$\mu$m].

Examples of compounds that can be refined by the refining method according to the present embodiment include, but are not limited to, febuxostat, terfenadine, indomethacin, ibuprofen, loxoprofen, caffeine, diclofenac, and carbamazepine. Examples of the solvent for dissolving a raw material of a compound include, but are not limited to, alcohol solvents, such as methanol, ethanol, 1-propanol, 2-propanol (isopropanol (IPA)), 1-butanol, 2-butanol, isobutanol, and tert-butanol; nitrile solvents, such as acetonitrile and propionitrile; ether solvents, such as diethyl ether and tetrahydrofuran; ketone solvents, such as acetone and methyl ethyl ketone; halogen solvents, such as dichloromethane and chloroform; ester solvents, such as ethyl acetate and methyl acetate; aliphatic hydrocarbon solvents, such as pentane, hexane, heptane, octane, and cyclohexane; aromatic hydrocarbon solvents, such as benzene, toluene, and xylene; and mixed solvents of alcohol solvents and water.

In the refining method according to the present embodiment, any infrared radiation apparatus capable of emitting infrared radiation including a wavelength $\lambda$ [$\mu$m] can be used. For example, the infrared radiation apparatus may include a sheet radiator and a planar heater serving as a heat source. The infrared radiation apparatus is preferably an infrared radiation apparatus capable of emitting infrared radiation having a peak at the wavelength $\lambda$ [$\mu$m], particularly infrared radiation having a peak at the wavelength $\lambda$ [$\mu$m] and having a narrow half-width. Examples of such an infrared radiation apparatus include metamaterial emitters and infrared radiation apparatuses with a filter. Examples of the metamaterial emitters include emitters of a metal-insulator-metal (MIM) type, a microcavity type, a meta-atom type, and a multilayer type. Examples of the MIM type include those described in Reference 1 (JSME TED Newsletter, No. 74, pp. 7-10, 2014). The MIM type is described in detail later. Examples of the microcavity type and the meta-atom type include those described in Reference 2 (JSME TED Newsletter, No. 74, pp. 2-6, 2014). Examples of the multilayer type include those described in Reference 3 (ACS Cent. Sci., Vol. 5, pp. 319-326, 2019). Examples of the infrared radiation apparatuses with a filter include infrared heaters described in Japanese Patent No. 6442355.

Figure 2:
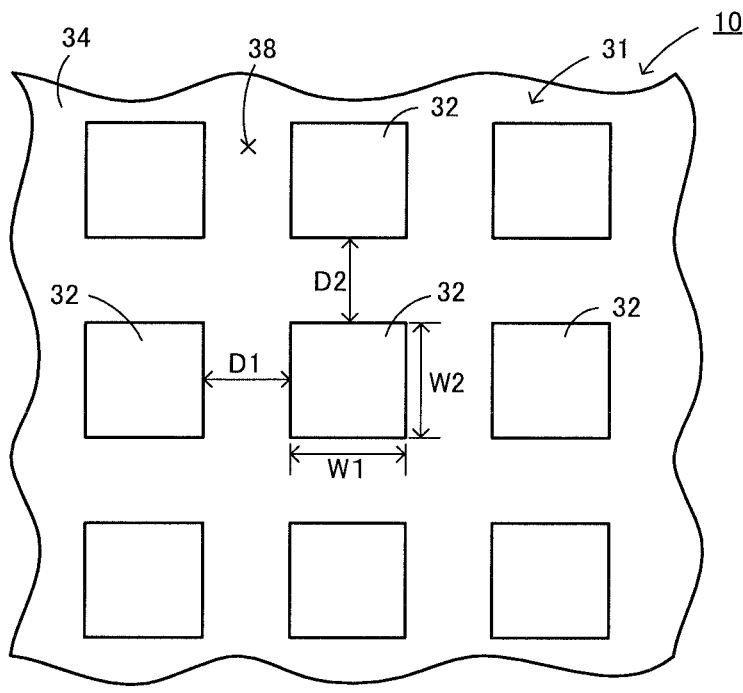
FIG. 2 is a partial bottom view of an infrared heater 10.

FIG. 1 is a perspective view of a refining apparatus 1 partially in cross section. FIG. 2 is a partial bottom view of an infrared heater 10. The horizontal direction, the front-back direction, and the vertical direction are as illustrated in FIG. 1.

The refining apparatus 1 is an apparatus for precipitating a specific crystal form from a solution 22 in a flat laboratory dish 20 using the infrared heater 10. The solution 22 contains a compound with a plurality of crystal forms dissolved in a solvent.

The infrared heater 10 is an example of a metamaterial emitter of the MIM type and includes a heater body 11, a structure 30, and a casing 70. The infrared heater 10 emits infrared radiation to the solution 22 in the flat laboratory dish 20 located under the infrared heater 10.

The heater body 11 is configured as a planar heater and includes a heating element 12 in which a linear member is bent in a zigzag, and a protective member 13, which is an insulator in contact with and surrounding the heating element 12. The material of the heating element 12 is, for example, W, Mo, Ta, an Fe—Cr—Al alloy, or a Ni—Cr alloy. The material of the protective member 13 is, for example, an insulating resin, such as a polyimide, or a ceramic. The heater body 11 is located inside the casing 70. Both ends of the heating element 12 are coupled to a pair of input terminals (not shown) attached to the casing 70. Electric power can be supplied to the heating element 12 from the outside through the pair of input terminals. The heater body 11 may be a planar heater with a ribbon-like heating element wound around an insulator.

The structure 30 is a sheet radiator provided under the heating element 12. The structure 30 includes a first conductor layer 31 (a metal pattern), a dielectric layer 34, a second conductor layer 35 (a metal substrate), and a supporting substrate 37 stacked in this order from the outside to the inside under the infrared heater 10. The structure 30 is located so as to close an opening in the lower portion of the casing 70.

As illustrated in FIG. 2, the first conductor layer 31 is configured as a metal pattern with a periodic structure in which metal electrodes 32 of the same shape and size are arranged at regular intervals on the dielectric layer 34. More specifically, the first conductor layer 31 is configured as a metal pattern in which a plurality of tetragonal metal electrodes 32 are arranged at regular intervals D1 in the horizontal direction and at regular intervals D2 in the front-back direction on the dielectric layer 34. The metal electrodes 32 have a shape with a thickness (a vertical height) smaller than a lateral width W1 (a width in the horizontal direction) and a longitudinal width W2 (a width in the front-back direction). The metal pattern has a transverse period $\Lambda 1 = D1 + W1$ and a longitudinal period $\Lambda 2 = D2 + W2$. It is assumed that D1 and D2 are the same, and W1 and W2 are the same. The material of the metal electrodes 32 is, for example, gold or aluminum (Al). The metal electrodes 32 are bonded to the dielectric layer 34 via an adhesive layer (not shown). The material of the adhesive layer is, for example, chromium (Cr), titanium (Ti), or ruthenium (Ru).

The dielectric layer 34 is a flat member with an upper surface bonded to the second conductor layer 35. The dielectric layer 34 is located between the first conductor layer 31 and the second conductor layer 35. A portion of the lower surface of the dielectric layer 34 on which the metal electrodes 32 are not located is a radiation surface 38 for emitting infrared radiation to an object. The material of the dielectric layer 34 is, for example, alumina ($Al_2O_3$) or silica ($SiO_2$).

The second conductor layer 35 is a metal sheet with an upper surface bonded to the supporting substrate 37 via an adhesive layer (not shown). The material of the second conductor layer 35 may be the same as the material of the first conductor layer 31. The material of the adhesive layer is, for example, chromium (Cr), titanium (Ti), or ruthenium (Ru).

The supporting substrate 37 is a flat member fixed inside the casing 70 with a fixing component or the like (not shown) and supports the first conductor layer 31, the dielectric layer 34, and the second conductor layer 35. The material of the supporting substrate 37 is, for example, a material, such as a Si wafer or glass, that can easily maintain a smooth surface, has high heat resistance, and has low thermal warping. The supporting substrate 37 may be in contact with the lower surface of the heater body 11 or may be separated from the lower surface with a space therebetween. When the supporting substrate 37 is in contact with the heater body 11, they may be bonded together.

The structure 30 functions as a metamaterial emitter with the characteristics of selectively emitting infrared radiation of a specific wavelength. The characteristics probably result from a resonance phenomenon explained by magnetic polariton. The magnetic polariton is a resonance phenomenon in which a confinement effect of a strong electromagnetic field can be produced in a dielectric (the dielectric layer 34) between two upper and lower conductors (the first conductor layer 31 and the second conductor layer 35). Thus, in the structure 30, a portion of the dielectric layer 34 between the second conductor layer 35 and the metal electrodes 32 serves as an infrared radiation source. Infrared radiation emitted from the radiation source goes around the metal electrodes 32 and is emitted to the surrounding environment from a portion of the dielectric layer 34 on which the metal electrodes 32 are not located (that is, from the radiation surface 38). In the structure 30, the materials of the first conductor layer 31, the dielectric layer 34, and the second conductor layer 35 and the shape and periodic structure of the first conductor layer 31 can be adjusted to regulate the resonance wavelength. Thus, infrared radiation emitted from the radiation surface 38 of the structure 30 characteristically has high emissivity at a specific wavelength. In the present embodiment, the material, shape, periodic structure, and the like are adjusted so that the structure 30 characteristically emits from the radiation surface 38 infrared radiation having a maximum peak with a half-width of 2.0 μm or less (preferably 1.5 μm or less, more preferably 1.0 μm or less) and with an emissivity of 0.7 or more (preferably 0.8 or more) in the wavelength range of 0.9 to 25 μm (preferably 2.5 to 25 μm (4000 to 400 cm$^{-1}$)). Thus, the structure 30 characteristically emits infrared radiation having a sharp maximum peak with a relatively small half-width and a relatively high emissivity. The half-width is, for example, but not limited to, preferably 2.0 μm or less, more preferably 1.5 μm or less, still more preferably 1.0 μm or less.

The casing 70 has an approximately rectangular parallelepiped shape with a space therein and with an open bottom surface. The heater body 11 and the structure 30 are located in the space inside the casing 70. The casing 70 is formed of a metal (for example, stainless steel or aluminum) to reflect infrared radiation emitted from the heating element 12.

An example of use of the refining apparatus 1 is described below. As described above, a specific crystal form is precipitated from the solution of the organic compound X with four crystal forms a1, a2, b1, and b2 dissolved in the solvent. Precipitation of the crystal form a1 is described below as an example.

First, the flat laboratory dish 20 containing the solution 22 is placed under the first conductor layer 31 of the infrared heater 10. The solution 22 contains the organic compound X dissolved in the solvent p1. Next, electric power is supplied from a power supply (not shown) through an input terminal to both ends of the heating element 12. The electric power is supplied so that the temperature of the heating element 12 reaches a preset temperature (for example, but not limited to, several hundred degrees Celsius). The heating element 12 heated to the predetermined temperature transfers energy to the surroundings by at least one of three heat transfer modes of conduction, convection, and radiation and heats the structure 30. Consequently, the structure 30 is heated to a predetermined temperature, becomes a secondary radiator, and emits infrared radiation.

In this case, a predetermined wavelength $\lambda 1$ [μm] is set as a target wavelength, and infrared radiation having a peak at the wavelength $\lambda 1$ [μm] is set to be emitted from the structure 30. More specifically, the intervals D1 and D2 of the metal electrodes 32 of the structure 30, the widths W1 and W2 of the metal electrodes 32, and the periods $\Lambda 1$ and $\Lambda 2$ of the metal pattern are set so that infrared radiation emitted from the structure 30 has a peak at a predetermined wavelength $\lambda 1$ [μm]. Irradiation of the solution 22 in the flat laboratory dish 20 with infrared radiation having a peak at the wavelength $\lambda 1$ [μm] evaporates the solvent p1 of the solution 22 with the passage of time and finally selectively precipitates crystals of the organic compound X with the crystal form a1.

Although the infrared heater 10 is designed to mainly emit infrared radiation of a target wavelength, it is difficult to remove all radiation other than the target wavelength from the infrared radiation of the structure 30, and convective heat dissipation from components of the heater to the surroundings will occur in the atmosphere. To form an actual process, therefore, various considerations should be given to the shape of the apparatus and the like so that such associated heat flow does not excessively increase the temperature of raw materials and the like.

The refining method according to the present embodiment described in detail above can precipitate a specific crystal form from a solution of a compound dissolved in a solvent by adjusting the solvent for dissolving the compound and a peak wavelength of infrared radiation emitted to the solution. Furthermore, the use of the infrared heater 10 of the MIM type allows a peak wavelength of emitted infrared radiation to be designed to accurately match a target wavelength. The first conductor layer 31 of the infrared heater 10 is configured as a metal pattern with a periodic structure in which the metal electrodes 32 of the same shape and size are arranged at regular intervals. The infrared heater 10 emits infrared radiation having a peak wavelength that changes with the lateral width W1 and the longitudinal width W2 of the metal electrodes 32. The lateral width W1 and the longitudinal width W2 of the metal electrodes 32 can be accurate as designed, for example, by drawing and lift-off using a well-known electron-beam lithography system. Thus, a peak wavelength of infrared radiation emitted from the infrared heater 10 can be relatively easily and accurately adjusted to a target wavelength.

It goes without saying that the present invention should not be limited to these embodiments and can be implemented in various aspects within the technical scope of the present invention.

The metal electrodes 32 are tetragonal in these embodiments but may be circular. In circular metal electrodes 32, the diameter corresponds to the lateral width W1 and the longitudinal width W2.

EXAMPLES

[Basic Information]
Dissolution Rate

The dissolution time of the raw material of febuxostat in a solvent was examined as described below. The solvent was ethanol, 2-propanol, or acetonitrile. First, a heating stage (FP80HT, Mettler) was installed in a stereoscopic microscope (SZX16, Olympus Corporation), and the surface temperature of the heating stage was maintained at 50±5° C. 25 mg of febuxostat (product code F0847, Tokyo Chemical Industry Co., Ltd.) was weighed into a flat laboratory dish (φ32 mm×16 mm), and 2 mL of the solvent was weighed and added to the laboratory dish, which was then immediately covered with a glass lid. The laboratory dish was placed on the heating stage. The dissolution time was defined as the time from the point in time when the laboratory dish was placed to the point in time when no undissolved febuxostat in the solvent was observed with the stereoscopic microscope. As a result, the dissolution time was ethanol<2-propanol<acetonitrile (in other words, the dissolution rate was ethanol>2-propanol>acetonitrile). Table 1 shows the results.

The dissolution times of the raw materials of loxoprofen and diclofenac in the solvents were also examined in the same manner as febuxostat. Table 1 shows the results.

TABLE 1

| Compounds | Dissolution rate of the raw material (Arranged in order from the fastest to the slowest) |
| --- | --- |
| Febuxostat | Ethanol, 2-propanol, Acetonitrile |
| Loxoprofen | Ethanol, 2-propanol |
| Diclofenac | Ethanol, Ethanol/IPA[X1] |

[X1]Ethanol/IPA is mixed solvents of ethanol:IPA = 50:50 (volume ratio)

Infrared Absorption Spectrum

Figure 3:
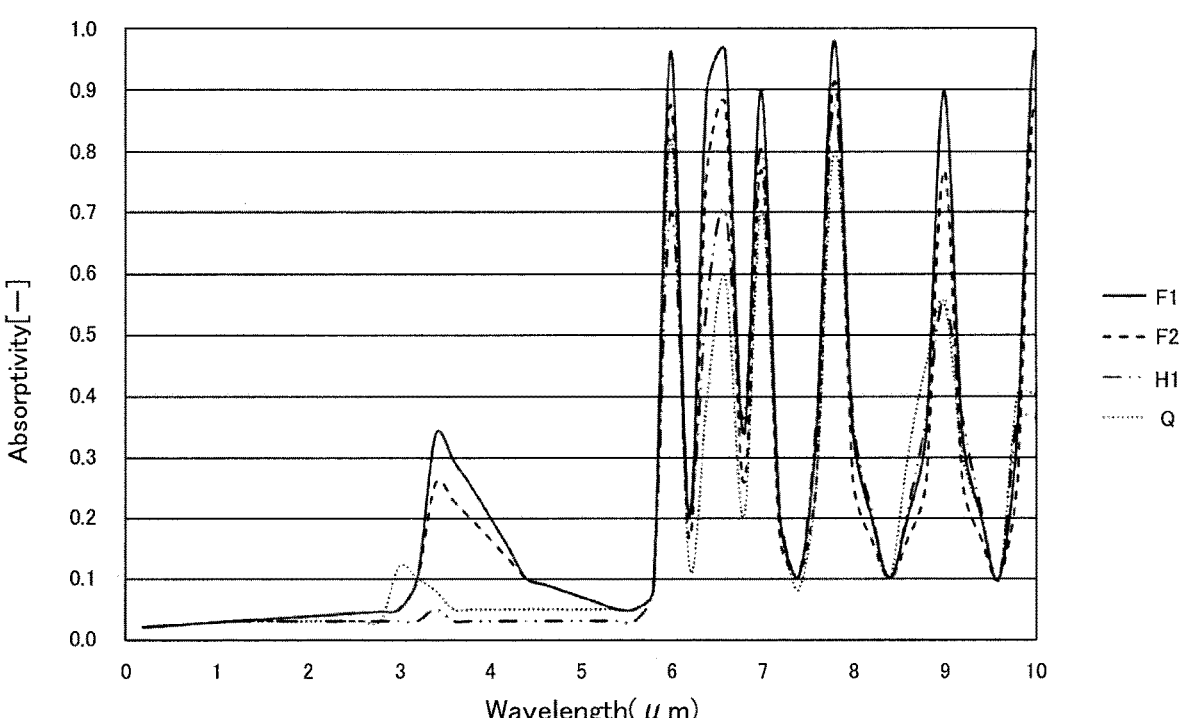
FIG. 3 is a graph of an infrared absorption spectrum of febuxostat.
Figure 4:
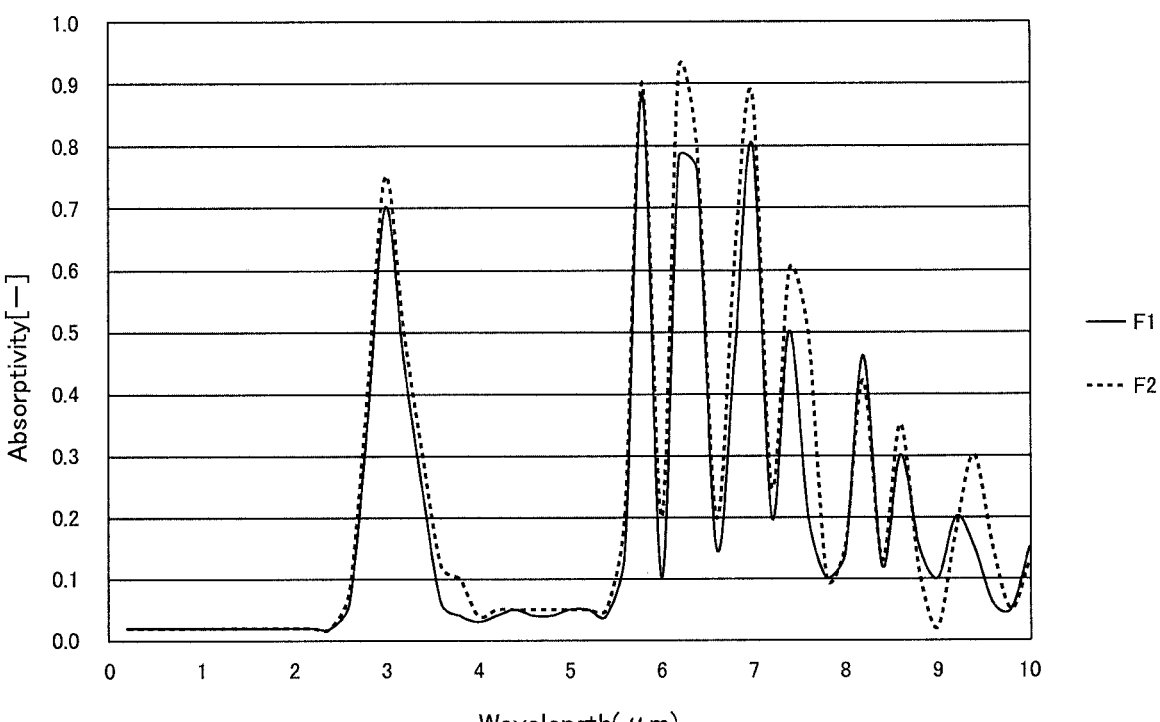
FIG. 4 is a graph of an infrared absorption spectrum of loxoprofen.
Figure 5:
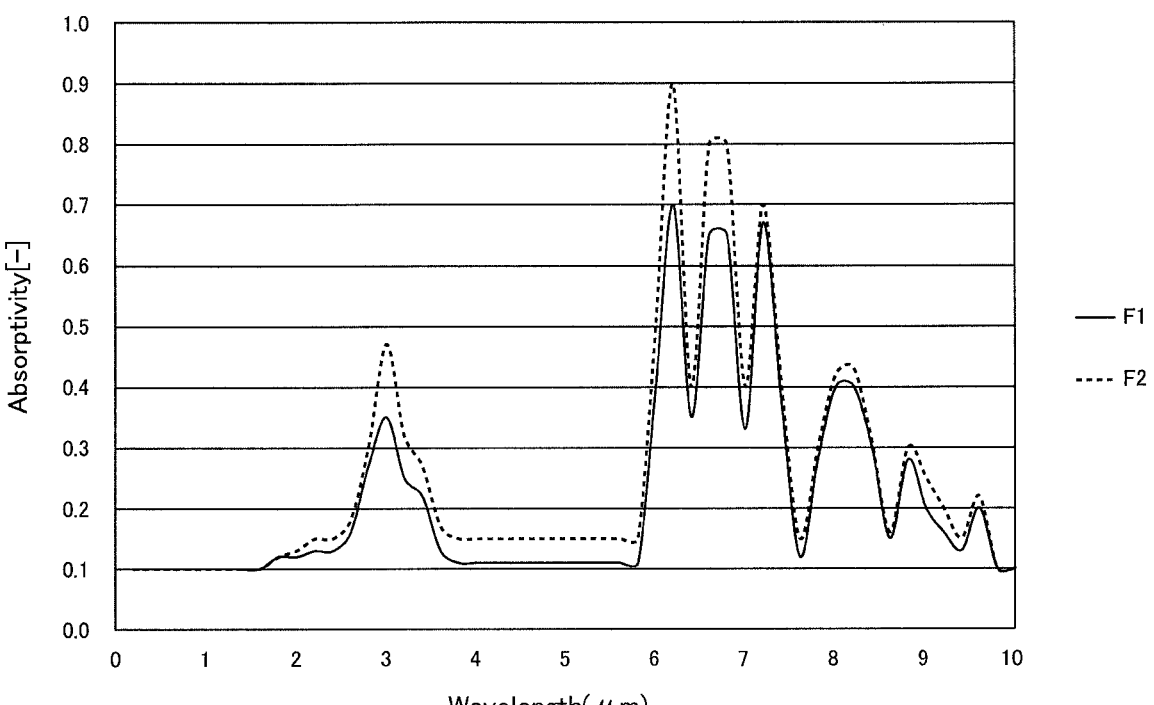
FIG. 5 is a graph of an infrared absorption spectrum of diclofenac.

Febuxostat is known to have a plurality of crystal forms F1, F2, Q, and H1. FIG. 3 is a graph of an infrared absorption spectrum of each crystal form. Loxoprofen is known to have crystal forms F1 and F2. FIG. 4 is a graph of an infrared absorption spectrum of each crystal form. Diclofenac is known to have crystal forms F1 and F2. FIG. 5 is a graph of an infrared absorption spectrum of each crystal form. Table 2 shows absorptivities at the wavelengths of 3.7 μm and 6.7 μm of the infrared absorption spectrum of each crystal form of febuxostat, loxoprofen, and diclofenac.

TABLE 2

| Compounds | Crystals | Absorptivity (−) | |
| --- | --- | --- | --- |
| | | 3.7(μm) | 6.7(μm) |
| Febuxostat | F1 | 0.27 | 0.65 |
| | F2 | 0.21 | 0.56 |
| | Q | 0.05 | 0.40 |
| | H1 | 0.03 | 0.53 |
| Loxoprofen | F1 | 0.06 | 0.40 |
| | F2 | 0.10 | 0.55 |
| Diclofenac | F1 | 0.12 | 0.65 |
| | F2 | 0.15 | 0.80 |

Example 1

A test sample was prepared by weighing 25 mg of febuxostat (product code F0847, Tokyo Chemical Industry Co., Ltd.) into a flat laboratory dish (032 mm×16 mm), adding 1 mL of ethanol (Kanto Chemical Co., Inc.), heating the febuxostat on a hot plate at 80° C. for 2 minutes, and dissolving the febuxostat with slight stirring. The test sample was irradiated with infrared radiation including a wavelength of 3.7 μm (infrared radiation having a peak at a wavelength of 3.7 μm) (a radiation source temperature of 400° C.) for 30 minutes to evaporate the solvent and precipitate crystals. Infrared radiation was emitted from the infrared heater 10 of the MIM type. The first conductor layer 31 (the metal electrodes 32) made of Au had a height h of 100 nm. The dielectric layer 34 made of $Al_2O_3$ had a thickness d of 100 nm. The second conductor layer 35 made of Au had a height f of 200 nm. The metal electrodes 32 had a lateral width W1 and a longitudinal width W2 of 840 nm. The intervals D1 and D2 were 1160 nm. The periods Λ1 and Λ2 were 2000 nm. Infrared radiation (half-width: 0.5 μm) having a peak at a wavelength of 3.7 μm was emitted. The crystal form of the precipitated crystals was identified as F1 by XRD analysis. The XRD analysis was performed with an X-ray diffractometer (product name: Ultima IV, Rigaku).

Example 2

A test sample was prepared in the same manner as in Example 1 except that infrared radiation including a wavelength of 6.7 μm (infrared radiation having a peak at a wavelength of 6.7 μm) was used instead of the infrared radiation including a wavelength of 3.7 μm, and the crystal form was identified by XRD analysis. The crystal form was F2. In Example 2, the first conductor layer 31 (a layer having circular metal electrodes 32) of the infrared heater 10 had a height h of 50 nm. The dielectric layer 34 had a thickness d of 190 nm. The second conductor layer 35 had a height f of 100 nm. The circular metal electrodes 32 had a diameter (corresponding to W1 and W2) of 2.16 μm. The intervals between the metal electrodes (corresponding to D1 and D2) were 1.84 μm. The period (corresponding to Λ1 and Λ2) was 4.0 μm. Infrared radiation having a peak at a wavelength of 6.7 μm (half-width: 0.5 μm) was emitted.

Example 3

A test sample was prepared in the same manner as in Example 1 except that 1 mL of 2-propanol (Sigma-Aldrich Corporation) was used instead of 1 mL of ethanol, and the crystal form was identified by XRD analysis. The crystal form was H1.

Example 4

A test sample was prepared in the same manner as in Example 1 except that 2 mL of acetonitrile (Kishida Chemical Co., Ltd.) was used instead of 1 mL of ethanol and that infrared radiation having a peak at a wavelength of 6.7 μm was used instead of the infrared radiation having a peak at a wavelength of 3.7 μm, and the crystal form was identified by XRD analysis. The crystal form was Q.

The results of Examples 1 to 4 are summarized in Table 3.

TABLE 3

| Examples | Solvent | Wavelength (μm) | Crystal forms of febuxostat |
|---|---|---|---|
| 1 | Ethanol | 3.7 | F1 |
| 2 | | 6.7 | F2 |
| 3 | 2-propanol | 3.7 | H1 |
| 4 | Acetonitrile | 6.7 | Q |

Examples 1 and 2 show that, even in the same solvent, infrared radiation with different peak wavelengths precipitated febuxostat of different crystal forms. Examples 1 and 3 and Examples 2 and 4 show that, even with infrared radiation with the same peak wavelength, febuxostat of different crystal forms precipitated in different solvents.

These examples show that the combination of the solvent and the peak wavelength of infrared radiation may be determined depending on the crystal form to be precipitated among the four crystal forms F1, F2, H1, and Q. More specifically, to precipitate febuxostat of the crystal form F1, as described in Example 1, ethanol may be used as a solvent, and infrared radiation with a peak wavelength of 3.7 μm may be emitted. To precipitate febuxostat of the crystal form F2, as described in Example 2, ethanol may be used as a solvent, and infrared radiation with a peak wavelength of 6.7 μm may be emitted. To precipitate febuxostat of the crystal form H1, as described in Example 3, 2-propanol may be used as a solvent, and infrared radiation with a peak wavelength of 3.7 μm may be emitted. To precipitate febuxostat of the crystal form Q, as described in Example 4, acetonitrile may be used as a solvent, and infrared radiation with a peak wavelength of 6.7 μm may be emitted.

The order of stability of the crystal form of febuxostat is F1>F2>Q>H1. Febuxostat of F1 is considered to be a crystal form with highest stability, that is, the most stable form. In general, the most stable form is less soluble in solvents than the other crystal forms. Thus, in a solvent with a high dissolution rate, the most stable form is basically precipitated. In other words, to precipitate the most stable form, a solvent with a high dissolution rate is preferably used. The other crystal forms are more soluble than the most stable form and are therefore less likely to precipitate than the most stable form in a solvent with a high dissolution rate. With respect to wavelength, a wavelength at which the most stable form has lower absorptivity is selected to precipitate the most stable form. As shown in FIG. 3, the absorption spectrum of the most stable form F1 has higher absorptivity than the other crystal forms at all wavelengths. Among them, a wavelength of 3.7 μm, at which the absorptivity is relatively low, is selected. At a wavelength of 3.7 μm, F2 also has some absorptivity and is considered to be partly prevented from precipitate. Thus, to selectively precipitate febuxostat of the most stable form F1, the solvent should be ethanol, which has a high dissolution rate, and the wavelength should be 3.7 μm, at which the absorptivity is relatively low.

Febuxostat of H1 is considered to be a crystal form with lowest stability, that is, a metastable form. In general, the metastable form is more soluble in solvents than the other crystal forms. Thus, the metastable form is less likely to precipitate than the other crystal forms unless a solvent with a low dissolution rate is used to increase the degree of supersaturation. In other words, to precipitate the metastable form, a solvent with a low dissolution rate is preferably used. With respect to wavelength, a wavelength at which the metastable form has lower absorptivity and at which the other crystal forms have higher absorptivity is selected to precipitate the metastable form. This activates the thermal vibrations of the other crystal forms, reduces the number of crystal nuclei of the other crystal forms, and reduces the amount of precipitate of the other crystal forms. The absorption spectrum of each crystal form in FIG. 3 shows that the infrared radiation with a wavelength of 3.7 μm is less likely to be absorbed by the metastable form H1 and is easily absorbed by the other crystal forms. Thus, to selectively precipitate febuxostat of the metastable form H1, the solvent should be 2-propanol, which has a low dissolution rate, and the wavelength should be 3.7 μm, at which the absorptivity is lower than those of the other crystal forms.

Febuxostat of F2 and Febuxostat of Q have intermediate stability between the metastable form H1 and the most stable form F1. Thus, the dissolution rate and the wavelength of infrared radiation are preferably intermediate between H1 and F1.

Example 5

A test sample was prepared by weighing 25 mg of loxoprofen (product code L0244, Tokyo Chemical Industry Co., Ltd.) into a flat laboratory dish (032 mm×16 mm), adding 1 mL of 2-propanol, heating the loxoprofen on a hot plate at 80° C. for 1 minute, and dissolving the febuxostat with slight stirring. The test sample was irradiated with infrared radiation including a wavelength of 6.7 μm (infrared radiation having a peak at a wavelength of 6.7 μm) to evaporate the solvent and precipitate crystals. The crystal form of the precipitated crystals was identified as F1 by XRD analysis.

Example 6

Crystals were precipitated in the same manner as in Example 5 except that ethanol was used as a solvent instead of 2-propanol and that infrared radiation including a wavelength of 3.7 μm (infrared radiation having a peak at a wavelength of 3.7) was used instead of the infrared radiation including a wavelength of 6.7 μm. The crystal form of the precipitated crystals was identified as F2 by XRD analysis.

The results of Examples 5 and 6 are summarized in Table 4.

TABLE 4

| Examples | Solvent | Wavelength (μm) | Crystal forms of Loxoprofen |
|---|---|---|---|
| 5 | 2-propanol | 6.7 | F1 |
| 6 | Ethanol | 3.7 | F2 |

Examples 5 and 6 show that the combination of the solvent and the peak wavelength of infrared radiation may be determined depending on the crystal form to be precipitated among the two crystal forms F1 and F2 of loxoprofen. More specifically, to precipitate loxoprofen of the crystal form F1, 2-propanol may be used as a solvent, and infrared radiation with a peak wavelength of 6.7 μm may be emitted. To precipitate loxoprofen of the crystal form F2, ethanol may be used as a solvent, and infrared radiation with a peak wavelength of 3.7 μm may be emitted.

The order of stability of the crystal form of loxoprofen is F2>F1. F2 is considered to be the most stable form, and F1 is considered to be the metastable form. To precipitate the most stable form, a solvent with a high dissolution rate is preferably used, and a wavelength at which the most stable form has lower absorptivity is preferably selected. Thus, to selectively precipitate loxoprofen of the most stable form F2, the solvent should be ethanol, which has a high dissolution rate, and the wavelength should be 3.7 μm, at which the absorptivity is relatively low. To precipitate the metastable form, a solvent with a low dissolution rate is preferably used, and a wavelength at which the metastable form has lower absorptivity and at which the other crystal forms have higher absorptivity is preferably selected. Thus, to selectively precipitate loxoprofen of the metastable form F1, the solvent should be 2-propanol, which has a low dissolution rate, and the wavelength should be 6.7 μm, at which the absorptivity is lower than those of the other crystal forms.

Example 7

A test sample was prepared by weighing 25 mg of diclofenac (product code D3748, Tokyo Chemical Industry Co., Ltd.) into a flat laboratory dish (032 mm×16 mm), adding 1 mL of a mixed solvent (ethanol:2-propanol (IPA) =50:50 (volume ratio)), heating the diclofenac on a hot plate at 80° C. for 1 minute, and dissolving the diclofenac with slight stirring. The test sample was irradiated with infrared radiation including a wavelength of 6.7 μm (infrared radiation having a peak at a wavelength of 6.7 μm) to evaporate the solvent and precipitate crystals. The crystal form of the precipitated crystals was identified as F1 by XRD analysis.

Example 8

Crystals were precipitated in the same manner as in Example 7 except that ethanol was used as a solvent instead of the mixed solvent and that infrared radiation including a wavelength of 3.7 μm (infrared radiation having a peak at a wavelength of 3.7) was used instead of the infrared radiation including a wavelength of 6.7 μm. The crystal form of the precipitated crystals was identified as F2 by XRD analysis.

The results of Examples 7 and 8 are summarized in Table 5.

TABLE 5

| Examples | Solvent | Wavelength (μm) | Crystal forms of Diclofenac |
|---|---|---|---|
| 7 | Ethanol/IPA | 6.7 | F1 |
| 8 | Ethanol | 3.7 | F2 |

※1 Ethanol/IPA is mixed solvents of ethanol:IPA = 50:50 (volume ratio)

Examples 7 and 8 show that the combination of the solvent and the peak wavelength of infrared radiation may be determined depending on the crystal form to be precipitated among the two crystal forms F1 and F2 of diclofenac.

More specifically, to precipitate diclofenac of the crystal form F1, ethanol:IPA=50:50 (volume ratio) may be used as a solvent, and infrared radiation with a peak wavelength of 6.7 μm may be emitted. To precipitate diclofenac of the crystal form F2, ethanol may be used as a solvent, and infrared radiation with a peak wavelength of 3.7 μm may be emitted.

The order of stability of the crystal form of diclofenac is F2>F1. F2 is considered to be the most stable form, and F1 is considered to be the metastable form. To precipitate the most stable form, a solvent with a high dissolution rate is preferably used, and a wavelength at which the most stable form has lower absorptivity is preferably selected. Thus, to selectively precipitate diclofenac of the most stable form F2, the solvent should be ethanol, which has a high dissolution rate, and the wavelength should be 3.7 μm, at which the absorptivity is relatively low. To precipitate the metastable form, a solvent with a low dissolution rate is preferably used, and a wavelength at which the metastable form has lower absorptivity and at which the other crystal forms have higher absorptivity is preferably selected. Thus, to selectively precipitate diclofenac of the metastable form F1, the solvent should be ethanol:IPA=50:50 (volume ratio), which has a low dissolution rate, and the wavelength should be 6.7 μm, at which the absorptivity is lower than those of the other crystal forms.

The present application claims priority from International Application No. PCT/JP2020/027266, filed on Jul. 13, 2020, the entire contents of which are incorporated herein by reference.

What is claimed is:

1. A refining method for crystallizing a compound with a plurality of crystal forms, comprising:
   setting, as a target wavelength, a specific infrared wavelength at which a specific crystal form of the plurality of crystal forms precipitates from a solution of the compound dissolved in a solvent; and using an infrared radiation apparatus capable of emitting infrared radiation including the target wavelength to evaporate the solvent and precipitate the specific crystal form while irradiating the solution with infrared radiation including the target wavelength,
   wherein the specific infrared wavelength is set as the target wavelength based on an infrared absorption spectrum of the crystal form and a dissolution rate of the compound in the solvent, and
   wherein the dissolution rate is a time to dissolve the compound in the solvent, which is determined before performing the refining method.

2. The refining method according to claim 1, wherein the specific infrared wavelength is set as the target wavelength based on stability of the crystal form, an infrared absorption spectrum of the crystal form, and a dissolution rate of the compound in the solvent.

3. The refining method according to claim 1, wherein the infrared radiation apparatus includes a sheet radiator and a planar heater serving as a heat source.

4. The refining method according to claim 1, wherein the infrared radiation apparatus can emit infrared radiation having a peak at the target wavelength.

5. The refining method according to claim 4, wherein the infrared radiation apparatus emits infrared radiation having a peak at the target wavelength from a structure composed of a metal pattern, a dielectric layer, and a metal substrate stacked in this order from the outside to the inside, the metal pattern includes metal electrodes of the same shape and size arranged at regular intervals on the dielectric layer, and a peak wavelength of the infrared radiation changes depending on a width of the metal electrodes.

6. The refining method according to claim 1, wherein the compound is febuxostat, loxoprofen, or diclofenac.

* * * * *